(12) United States Patent
Hansen et al.

(10) Patent No.: US 6,994,794 B2
(45) Date of Patent: Feb. 7, 2006

(54) MEDIA WITH GERMICIDAL PROPERTIES

(75) Inventors: Christopher B. Hansen, Newbury, OH (US); Samuel Mason, Wickliffe, OH (US); Mohan L. Sanduja, Flushing, NY (US); Carl Horowitz, Brooklyn, NY (US); Paul Thottathil, New Hyde Park, NY (US); Felicia Dragnea, Forest Hills, NY (US)

(73) Assignee: Kinetico Incorporated, Newbury, OH (US)

( * ) Notice: Subject to any disclaimer, the term of this patent is extended or adjusted under 35 U.S.C. 154(b) by 142 days.

(21) Appl. No.: 10/432,557

(22) PCT Filed: Nov. 27, 2001

(86) PCT No.: PCT/US01/44421

§ 371 (c)(1),
(2), (4) Date: May 22, 2003

(87) PCT Pub. No.: WO02/42215

PCT Pub. Date: May 30, 2002

(65) Prior Publication Data

US 2004/0050799 A1      Mar. 18, 2004

Related U.S. Application Data

(63) Continuation-in-part of application No. 09/722,911, filed on Nov. 27, 2000, now Pat. No. 6,471,876.

(51) Int. Cl.
*C02F 1/50*      (2006.01)

(52) U.S. Cl. .................. 210/764; 210/502.1; 210/504; 252/175

(58) Field of Classification Search ................ 210/764, 210/502, 504; 252/175
See application file for complete search history.

(56) References Cited

U.S. PATENT DOCUMENTS

| 4,111,713 A | * | 9/1978 | Beck .......................... 106/409 |
| 4,725,390 A | * | 2/1988 | Laird et al. ................. 264/660 |
| 4,996,872 A | * | 3/1991 | Mueller et al. ................ 73/38 |

* cited by examiner

*Primary Examiner*—Betsey Morrison Hoey
(74) *Attorney, Agent, or Firm*—Watts Hoffmann Co., L.P.A.

(57) ABSTRACT

Filtration media having germicidal for use in filtering particles and deactivating, removing and/or destroying microorganisms from a feed liquid passing through the media. The filtration media includes an effective amount of at least one germicidal agent associated to monomers polmerized and chemically grafted and covalently bonded to the surface of the media. The germicidal filter media is prepared by contacting the media with a grafting solution comprising one or more monomers, a catalyst, a surface agent, a curign agent, at least one graft initiator, and at least on germicide and subsequently curing the media at an elevated temperature to chemically graft the polmerizable monomers onto a surface of the media and associate at least one germicide thereto. Filter media suitable for use in the present invention include ceramic spheroids, hollow glass spheres, polmeric type meida, thermoset coated glass spheres, and crystalline microporous materials, such as zeolites. The germicidal filter media is effective for deactivating, destroying and/or removing from a feed liquid, such as water, escherichia coli, salmonella choleraesuis, staphylococcus, aspergillus, klebisiella, listeria, clostridium, rotavirus, cysts and other microorganisms. Moreover, the filter media can be used repeatedly without a significant decrease in its germicidal effectiveness.

31 Claims, No Drawings

MEDIA WITH GERMICIDAL PROPERTIES

RELATED APPLICATION

This application is a Continuation-in-Part of application Ser. No. 09/722,911 entitled, "FILTER MEDIA WITH GERMICIDAL PROPERTIES," filed Nov. 27, 2000 now U.S. Pat. No. 6,471,876.

FIELD OF THE INVENTION

The present invention is directed to media with germicidal properties. In particular, the present invention is directed a filter media with germicidal properties that is intended for use in water treatment.

BACKGROUND OF THE INVENTION

For close to a century, microorganism content, e.g., bacteria and viruses, in municipal water supplies has been controlled through the addition of oxidative chemicals such as chlorine. This has proven effective in control of most microorganisms and is easily monitored. For example, a residual capable of being measured is carried throughout the municipal distribution system and periodically monitored to insure that the drinking water supply has been effectively treated. However, these systems are not always reliable or readily available to remote areas. Moreover, when an oxidizing agent is used at the source point, there can be contamination away from the source caused by pipeline problems that could allow the water to be unsafe at the time it arrives at the final point of use. In addition, there are also growing health concerns surrounding some of the compounds formed from the use of oxidative chemicals in the water supply.

To address contamination away from the source, a variety of devices or methods can be utilized to remove, destroy or deactivate microorganisms at the point of use. These include boiling the water, exposing the water to ultraviolet light, use of ozone, addition of chemicals and others. Most, if not all, of the methods used to remove, destroy and/or deactivate microorganisms include the need for external energy or the addition of chemicals to the water.

None of the known methods typically used to remove, destroy and/or deactivate microorganisms at the point of use can be used to remove sediment or turbidity from the source water. Typically, conventional filtration apparatuses are used in combination with a process or apparatus to destroy, deactivate and/or remove microorganisms. The filtration apparatuses are utilized primarily for removing particles in order to reduce turbidity. Examples of typical water filtration media include sand, garnet and anthracite.

In addition to bacteria and viruses present in the source, otter microorganisms that can be harmful include protozoan cysts. Removal of harmful cysts is desired and is reflected in the EPA filtration requirements now mandated by the Surface Water Treatment Rule. Since some of these cysts are not destroyed and/or deactivated effectively by the typical chlorine dosages used in municipal application, filtration and the use of chemical coagulants are typically used. The chemical coagulants increase the size of the particles containing the cysts to a point at which they can be removed by conventional filtration. During coagulation, small particles are agglomerated into larger particles by adding the chemical coagulants to the source. Once agglomerates of a desired size are produced, the solution is passed through a filter to filter out the agglomerates.

However, chemical coagulation has several disadvantages. The mechanism for filtering the liquid is by physically straining particles from the feed solution, which are larger than can pass through interstices between grains of the media. The media can only remove particles that are larger than the interstices. For example, sand filters can only remove particles greater than about 20 microns in size. Eventually, the particles held by the media seal off the interstices, reducing filtration efficiency. Moreover, chemical coagulation does not necessarily remove or deactivate all of the microorganisms present in the source water. Chemical coagulation is also disadvantageous in view of the cost of the chemicals, the need to regulate the amount of chemicals despite a continuously changing feed stream and in view of a low flow rate. Disposing of chemical sludge waste is another concern Thus, there is a need for a method and apparatus that could simultaneously filter and disinfect a water supply without the need for external energy or addition of chemicals.

SUMMARY OF THE INVENTION

The present invention provides a new and improved filtration media having germicidal properties for use in filtering particles and simultaneously destroying, removing and/or deactivating microorganisms from a feed liquid passing therethrough. The present invention also provides a new and improved method for activating filtration media to give it germicidal properties. The filtration media comprises ceramic, polymeric and/or glass substrates to which polymerizable monomers are chemically grafted and bonded and to which at least one germicide, preferably two, is associated thereto. Modifications in the same fashion of other forms of ceramic, polymeric and/or glass media, such as porous materials, natural zeolites and fibrous filters, will be obvious to those skilled in the art. The polymerizable monomers and the germicides are present in a range of molar ratios, from ratios of 100:1 to 1:100, with a typical ratio about 1:1. Each germicide preferably has a minimum inhibitory concentration (MIC) less than about 1000 ppm (parts per million) for at least one targeted microorganism Preferably, the germicides include, but are not limited to, zinc pyrithione and diiodomethyl-p-tolylsulfone, but other germicides known to those skilled in the art may also be used. Preferably, the polymerizable monomers include but are not limited to vinyl, acrylic and epoxy resin monomers, that preferably includes a carboxyl group or sulfonyl group. Other monomers suitable for use in the present invention will be apparent to those skilled in the art in view of this disclosure. The primary monomer may be copolymerized with at least one secondary monomer. The amount of secondary monomer is at least 10 percent of the primary monomer. These materials are generally monomers, but may also be partially polymerized. These materials will undergo further polymerization under the proper reaction conditions.

In the polymerization reactions described above, the epoxy monomers are cross-linked with an amine curing agent. Furthermore, it has been found that the addition of an organic silane creates a bond to the surface of the media, enhancing the association of the polymerized monomers and germicides. Preparation of the germicidal media includes preparing a monomer grafting solution by uniformly mixing at least one germicide, at least one monomer, a polymerization initiating catalyst, a curing agent, and a surface agent. This grafting solution is then contacted with the substrate and allowed to coat the surface. The media is separated from the excess grafting solution, dried and then cured at an elevated temperature effective to chemically graft and covalently bond polymerizable monomers to which at least one germicide is associated to the surface of the media. Optionally, at least one other polymerizable monomer may co-polymerize with the germicide and monomer. The germicidal filter media is effective for treating a liquid by flowing the liquid across the germicidal filter media whereby the filter media removes particles. The germicide is present in an effective amount for destroying, removing and/or deactivating microorganisms in the water.

Other embodiments of the invention are contemplated to provide particular features and structural variants of the basic elements. The specific embodiments referred to as well as possible variations and the various features and advantages of the invention will become better understood when considered in connection with the detailed description that follows.

DETAILED DESCRIPTION OF PREFERRED EMBODIMENTS

The present invention is generally directed to filters having antimicrobial properties. In particular, filter media is contacted with a grafting solution wherein a polymer is grafted onto a surface of the filter media to which at least one germicide, preferably two, is associated thereto. The term "associated thereto" includes but is not limited van der Waals' forces (i.e. forces between atoms or molecules which are weaker than normal chemical bonds) covalent bonds, ionic bonds or any other means of chemical attraction known to those skilled in the art. Advantageously, filters including at least one layer of the germicidal filter media are effective for deactivating, destroying or removing microorganisms from a feed liquid such as water. The filtration media is preferably selected so that a wide range of particle sizes and specific gravities can be attained. U.S. patent application Ser. No. 89/361,719 filed Jul. 27, 1999, incorporated by reference in its entirety, discloses a filter gradient wherein the filter media is made entirely of the same material but differing with respect to its physical properties (i.e. specific gravity, particles size, particle shape, etc.). Thus, the present invention can advantageously be used in a wide variety of filter applications including its use in single layer, multi layer, upflow or downflow filtration configurations. Moreover, depending on the choice of germicides associated onto the filter media, the filter media, in addition to filtering particles, can be tailored to effectively remove, deactivate or destroy targeted bacteria, viruses or cysts present in the source feed liquid. This is especially desirable wherein the source feed liquid to be filtered is known to have undesirable levels of known microorganisms.

The materials suitable for use in the present invention as filter media include syntheic media such as ceramics, polymers, and glass and crystalline microporous materials such as zeolites. The media are preferably spherical or spheroidal but may be anhedral. The media are characterized by a generally coarse surface having a high surface area. A high surface area allows for the removal of smaller unwanted particulate matter. In view of this disclosure, other suitable filtration materials will become apparent to those skilled in the art.

The grafting solution comprises polymerizable monomers including at least one monomer, a catalyst, a curing agent, a surface agent and at least one graft initiator. The monomer is preferably a monomer having carboxyl groups. The polymerizable monomers and the germicides are present in a range of molar ratios, from ratios of 100:1 to 1: 100, with a typical ratio about 1:1.

Germicides are well known in the art. See, for instance, the section on "Quaternary Ammonium and Related Compounds" in the article on Antiseptics and Disinfectants" in Kirk-Othmer Encyclopedia of Chemical Technology 2nd Edition (vol. 2, pp. 632–635), hereby incorporated by reference in its entirety. Preferably, the germicide has a broad spectrum of antimicrobial and antifungal activity. Among the most common germicides are quaternary ammonium compounds such as benzethonium chloride. Others of this class (and generic formulas and descriptions thereof) are those mentioned, for instance in U.S. Pat. Nos. 2,984,639, 3,325,402, 3,703,583 and 3,431,208 and British Patent No. 1,319,396, all of which are incorporated by reference in their entirety. Usually one of the substituents on the quaternary nitrogen has a chain length of about 8 to 18 carbon atoms, for example, the quaternary ammonium compound alkyl dimethyl ethyl benzyl ammonium chloride, sold under the trade name BARQUAT 42502, manufactured by Lonza Chemicals.

Other types of germicides suitable for use in the present invention are the omadines. Examples of omadines are the substituted guanidines, e.g., chlorhexidene and the corresponding compounds having 2-ethylhexyl groups instead of chlorophenyl groups, and other bisguanidines such as those described in German Patent Application No. P2,332,382 published Jan. 10, 1974, incorporated by reference in its entirety. A preferred omadine is zinc pyrithione sold under the trade name ZINC OMADINE and manufactured by the Arch Chemical Company.

Other suitable germicides and equally preferred include diiodomethyl-p-tolylsulfone such as that sold under the trade name AMICAL 48 and manufactured by the Angus Chemical Company. Germicides diiodomethyl-p-tolylsulfone and zinc pyrithione are most preferred. In view of this disclosure, other germicides suitable for use in the present invention will be apparent to those skilled in the art.

The germicidal compound is preferably one which has germicidal activity such that its minimum inhibitory concentration (MIC) is below 1000 ppm, more preferably the MIC is below 500 ppm. The MIC is an indicator recognized by those skilled in the determination of the effectiveness of the germicide against certain known microorganisms. The MIC is determined by recognized procedures that measure the lowest concentration of a test antimicrobial compound that prevents the growth of a given culture of microorganisms under standardized conditions. It has been found that a MIC of less than 1000 ppm for a targeted microorganism is effective for removing, deactivating or destroying the microorganism. For example, the manufacturers of ZINC OMADINE and AMICAL 48 give the MICs as 4ppm and 6.2 ppm, respectively, for $S.$ $Aureus$ bacteria. As such, ZINC OMADINE and AMICAL 48 are highly effective for removing, deactivating or destroying this particular species of bacteria, among others, at concentrations equal to or greater than the MICs given.

Preferred polymerizable monomers are vinyl, acrylic and epoxy resin monomers that contain a carboxyl group or sulfonyl group. The primary monomer may be copolymerized with at least one secondary monomer. The amount of secondary monomer is at least 10 percent of the primary monomer. These materials are generally monomers, but may also be partially polymerized that will undergo further polymerization under the proper reaction conditions.

Among suitable monomers are those described in U.S. Pat. Nos. 2,984,639 and 3,325,402, incorporated herein by reference in their entirety. As indicated above, the monomers preferred are those which contain a sulfonyl or carboxyl functional group and are preferably those of the vinyl or acrylic type. Among these suitable monomers are ethylene imine, hydroxyethyl methacrylate, diethylamino ethylacrylate, dimethylaminoethyl methacrylate, ethylacrylate, butyl acrylate, as well as carboxylated and sulfonated vinyls such as vinyl chloride, vinyl pyrrolidine, vinylidene chloride, vinylidene bromide, etc. Other monomers suitable for use in the present invention will be apparent to those skilled in the art in view of this disclosure. Examples of suitable commercial monomers and prepolymers include those sold under the trade names, HYCAR 26288 manufactured by BF Goodrich Company, and SR-344 manufactured by Sartomer Company. Examples of suitable commercial epoxy resin monomers are EPON 828 and EPON 862 manufactured by Resolution Performance Products LLC. Examples of suitable commercial surface agents include those sold under the trade name AP SILANE manufactured by Advanced Polymer Incorporated. The preferred surface agent is AP Silane 99.

The method of grafting the monomers comprises contacting the filter media with a uniform solution of monomers, a catalyst, at least one graft initiator, a curing agent, and a surface agent. The graft initiator provides an active site on a surface of the filter media for reaction and forming a covalent bond with monomers. The graft initiator is selected to abstract an active hydrogen from a surface of the media to which the graft polymer will be bonded. The preferred graft initiator is a metal ion provided by the ionization of a metal salt. Silver ions provided by the ionization of silver salts are especially preferred although ferric and ferrous ions abstracted from iron salts as well as other metal salts may also be advantageously used. When a silver salt such as silver nitrate, silver perchlorate and silver acetate is used, such salts are preferably present in the graft solution in an amount of from about 0.001% to about 0.01% by weight of the solution.

The catalyst functions as a free radical initiator for polymerization of the monomer to occur according to reaction pathways well known in the art. Additionally, the selected catalyst may function to ionize the metal salts used as the grafting initiators. Suitable catalysts for effecting such a reaction include peroxides, peresters, peracids and persulfates. Preferred catalysts include hydrogen peroxide, methyl ethyl ketone peroxide, urea peroxide and ammonium persulfate. In view of this disclosure, other catalysts will be apparent to one ordinarily skilled in the art.

The curing agent functions to crosslink certain polymerized monomers and epoxy resin monomers. The preferred commercial curing agent in the present invention is sold under the trade name ANCAMINE BETA and manufactured by Air Products, Inc.

As indicated above, the filter media having germicidal properties is prepared by uniformly mixing in a suitable solvent at least one germicide, one or more monomers, at least one graft initiator, a surface agent and a catalyst. The filter media to be treated is then contacted with the liquid solution, allowed to remain in contact for a period of time and then separated from the excess liquid. The media is dried for about twenty-four hours and then cured for a period of time at an elevated temperature. The curing time and temperatures used are dependent on the various chemical entities chosen for the grafting solution and are well within the skills of those in the art to readily determine and optimize.

The resulting filter media has chemically grafted and covalently bonded thereto polymerizable monomers to which at least one germicide are associated, and is ready for use in a germicidal filter. Repeated experimentation has shown that the germicidal filter media retains its germicidal properties after repeated use indicating that the germicides are associated to the media.

Depending on the desired properties, the grafting solution can include more than one type of monomer, catalyst or grafting initiator. The amount of secondary monomer is at least 10 percent of the primary polymerizable monomer used in the liquid mixture. As a result, the actual molecule grafted onto the media may include more than one group of the second monomer. The polymerizable monomers and the germicides are present in a range of molar ratios, from ratios of 100:1 to 1:100, with a typical ratio about 1:1 in the liquid mixture.

The germicidal filter media is suitable for use in water filters including filters employing multiple layers of media for removing particulate matter from a liquid. The multiple layers of media can be made from the same or different synthetic materials. In the case of gradient filters, each layer of synthetic material preferably has a distinct particle size range and specific gravity range. The synthetic material can be formed of glass, ceramic, thermoset aggregates, thermoset coated materials, polymer particles, or any other suitable material and may be fabricated or otherwise classified to have different, predetermined specific gravities. Classification is less desirable since it is difficult to achieve both a desired particle size and intrinsic specific gravity in this manner compared to tailoring specific gravity during production of the material. As such, in addition to the more traditional downflow filter configurations, the media can be made for upflow filtration by tailoring the specific gravity of the media to be less than the specific gravity of the feed liquid. In view of this disclosure, other suitable filtration configurations utilizing the germicidal filter media will become apparent to those skilled in the art The media particle sizes are generally defined by the mesh size of a sieve in which the particles are screened. For example, a 30 mesh sieve will allow particles less than 600 micron to pass through the sieve, whereas particles 600 micron or larger than will not pass through. Generally, sieves of varying mesh ratings are stacked and particles are separated using methods well known to those skilled in the art. The range of particles separated is defined by the mesh size of the sieves used. For example, a mesh size designation of 20/40 means that substantially all particles have a size ranging from 20 to 40 mesh (841–420 micron in diameter). A 30/50 designation indicates that substantially all particles have a size ranging from 30 to 50 mesh (595–297 micron in diameter). The particle sizes of the present invention are preferably not larger than about 10 mesh (about 2000 micron in diameter) and, as small as about 80 mesh (about 177 micron in diameter). In multi-layer filter configurations, the mesh sizes are preferably chosen so that particle size ranges do not overlap between the filter media layers.

One type of filter media suitable for use in the present invention is made from polymeric and/or glass material. An example of this type of filter media suitable for use in the present invention are phenolic coated hollow glass spheres sold under the trade name SYNTREX and manufactured by the Kinetico Incorporated. The preparation of polymeric and/or glass gradient filter media suitable for use in the present invention has been described in U.S. Pat. 4,111,713, incorporated herein by reference in its entirety. Parts of the following discussion of materials and methods for making the polymer and glass filter media suitable for use in the present invention is from U.S. Pat. No. 4,111,713. Parting agent particles and either solid granules of liquefiable binder material or already liquid globules of binder material are tumbled together to form hollow spheres.

A wide variety of binder materials may be used to form the hollow spheres. More than one ingredient can be included in the binder material, although these ingredients will generally be dissolved or uniformly dispersed in one another. The result is that in a hollow sphere, as formed at the end of the sphere forming operation and solidification of the binder material, the sphere wall comprises only a single layer or thickness of the binder material, plus parting agent particles at least partially embedded in the layer or wall. There may be a gradation in the composition of the layer from one edge to the other edge; and there may be pigments, flow-control agents, fire retarding agents or other fillers (besides the parting agent) contained in the binder material as a discontinuous phase or dispersion. But the wall is a single-layer wall formed as a void develops in the liquid globule of binder material.

Illustrative organic ingredients of binder materials include epoxy resins; polycarbodiimides; formaldehyde resins such as phenol-formaldehydes, urea-formaldehydes and melamine-formaldehydes; polyesters; polyisocyanurates; polyurethanes; natural rubber and synthetic elastomers, such as silicones, styrene-butadiene copolymers; acrylic resins; ethylene copolymers such as ethylene-vinyl acetate copolymers; propylene copolymers such as ethylene-propylene copolymers; and olefin-wax combinations. These materials may be variously formulated to solidify, as by polymerization, by crosslinking, by loss of volatiles, or by cooling.

Inorganic binder materials such as the low melting glass described in U.S. Pat. No. 2,863,782, incorporated herein by reference in its entirety, may also be used. Glass-forming binder material granules may be provided as spray dried "slip" particles, prepared as in glaze or enamel preparation, which simplify incorporation of a volatile void forming agent. In the case of the ceramic or metal parting agents, the binder material may be a low-cost flux (such as sodium carbonate, sodium borate, or sodium silicate) and may be in the form of a water solution thickened to the proper viscosity with a material such as sodium alginate. This thickener acts as a temporary binder material prior to sintering the principal binder material.

During the sphere forming operation, the binder material should achieve a viscosity that is low enough for the parting agent particles to be wetted by the globules, and preferably low enough so that any cells forming inside an evacuated globule will tend to at least partially coalesce, whereby binder material will be concentrated at the exterior spherical wall or shell of the sphere. At the same time, the viscosity of the binder material should be high enough so that the expanded globule will not deform excessively while sphere formation is taking place. The useful range of viscosities for the binder material is broad, ranging from at least about 50 to 100,000 centipoise, but an especially preferred range is between about 100 and 1000 centipoise. The globules of binder material in the tumbling, sphere forming operation are termed liquid herein, since even when at high viscosity they are flowable. The range of useful viscosities will vary with particle size and the ease with which the parting agent particles can be wet. Surfactants can be used as an ingredient in the binder material or as a treatment on the parting agent particle.

In general any solid discrete free-flowing particulate material, which is sufficiently inert to retain its parting function throughout the sphere-forming operation, can be used as a parting agent particle. Examples of parting agent particles are hollow or solid glass microspheres; byproduct fines; ground scrap rubber particles such as vulcanized scrap rubber from tires; hard irregular abrasive particles such as aluminum oxide granules used for abrasive products; magnetic iron oxide particles; perlite; clay; glass fibers or glass flakes; wood flour, flame retardants such as aluminum trihydrate; organic polymeric particles and metal particles. Mixtures of any of the above particles can be used. For example, parting agent particles providing better flow properties may be mixed with irregular parting agent particles; or mixtures may be used to provide pigmentation, flame retardency, or variety in physical properties of the final sphere. Generally the parting agent particles will range from a few micrometers up to several hundred micrometers in size. They generally have a diameter no larger than the thickness of the wall of the final hollow sphere.

The void-forming agent used to form hollow spheres can be any substance, which, while present in the binder material, evolves a gas during the time and at a temperature of formation of the hollow spheres. It may be a separate ingredient added to the binder material; it may be a byproduct of a reaction of the binder material; or it may be a solvent or carrier for the binder material. Often the void forming agent is incorporated into the binder material while the latter is in liquid form prior to being solidified and formed into granules. In other cases it is mixed with milled solid inert material which is then spray dried or compressed or otherwise prepared into granules.

Most often the void forming agent causes an expansion in size of the liquid globules being formed into hollow spheres, since at least initially the outer wall of the globule tends to form voids of the desired size. Examples of useful void forming agents are: in the case of polycarbodiimide, a carbon dioxide reaction product of curing of the polycarbodiimide; in the case of some elastomers, a solvent for the elastomer precursor; in the case of low melting glass, water from hydrated borate or water contained in other "slip" particles.

The granules or globules of binder material introduced will vary in size depending upon the size of hollow sphere that is ultimately desired. Typically the granules are between 100 micrometers and 1 centimeter in diameter, and most often are less than 5 millimeters in diameter.

Generally binder material granules in such a range of sizes produce hollow spheres about ½ millimeter to 2 centimeters in diameter. Spheres can be made with good uniformity of sizes by using binder material granules or globules of uniform size. Further, hollow spheres may be screened after formation to provide desired ranges of sizes.

The hollow spheres formed have a single hollow interior space enclosed by a single spherical wall or shell. The coarse exterior wall or shell is characterized by having a high surface area. The hollow spheres are particularly useful as buoyant media for upflow gradient filter configurations. The media can easily be made to a wide variety of specific gravities depending on the size of the void created in the sphere and the densities of the raw materials used. Achieving different specific gravities can be found in examples 1–24 disclosed in U.S. Pat. No. 4,111,713 and would be apparent to one skilled in the art in view of this disclosure.

Another type of media suitable for use in the present invention are ceramic particles. Ceramic particles suitable for use in the present invention can be made with the materials and processes described in U.S. Pat. Nos. 4,725,390, 4,632,876, and 6,054,059, herein incorporated by reference in their entireties. Preferred ceramic media include media sold under the trade name MACROLITE, manufactured by the Kinetico Incorporated. The process for making the material generally includes the following steps. In the first step, binder, silicon carbide, mineral particulate and a metal oxide are mixed and spheroidized in order to form unfired spheroids. One example of suitable mineral particulates contains: 60% orthoclase, 10% nepheline, 10% hornblende, 5% diopside, 15% accessory minerals (titanite, apatite, magnetite and biotite) and trace amounts of secondary minerals (e.g. kaolinite and analcite). Another example contains approximately 75% plagioclase and orthoclase feldspar and 25% of the minerals pyroxene, hornblende, magnetite and quartz of which magnetite is less than 5%. Byproduct mineral fines of perlite (containing 2–5% chemically bound-water will also function as the mineral particulates. Minerals containing chemically bound water or sulfur which are useful components of the mineral particulates are: hornblende, apatite, biotite, pyrite, vermiculite and perlite.

Typical binders that may be useful as raw materials in the invention are bentonite (preferably sodium bentonite), starch, polyvinyl alcohol, cellulose gum, polyvinyl acetate and sodium lignosulphonate.

Silicon carbide raw material may conveniently be obtained as coproduct fines (less than 8 micrometers particle size) from the manufacture of silicon carbide abrasive products. It may alternatively be formed in situ, such as by adding a polycarbosilane solution to the mineral mixture, which would convert into SiC during processing.

Several types of mixing equipment may be used such as balling pans or disk spheroidizing machines. Machines known as high energy mixers are well suited to this application. Two examples of such machines are the Littleford mixer and the machine known as the Eirich machine. The Eirich machine is described in U.S. Pat. No. 3,690,622.

There are four basic steps in making the unfired spheroids in a high energy mixer: (1) mixing the dry powders at high speed rotation of the pan and an impacting impeller of the machine; (2) nucleation at which time water is added to the region of the mixer near the impacting impeller to be dispersed into droplets; (3) growth of the spheroids in the manner of a snow ball with the powder agglomerating during which time the impacting impeller rotates at a slower speed than it did during the nucleation step; and (4) polishing or smoothing the surfaces of the spheroids by turning off the impacting impeller and allowing the pan to rotate, similar to a balling pan. Polishing is optional and is less preferred for use in the present invention.

The amount of binder may generally comprise about 1–5% by weight of the dry materials fed to the mixer and is generally sufficient to permit screening and handling of the spheroids without significant attrition or breakage.

The wet spheroids are discharged from the mixer and dried at a temperature of about 40° C. to 200° C. The dried spheroids are then typically screened. The particle size range selected is actually smaller than the desired end product because of the growth of the spheroids during firing.

The dried spheroids are next mixed with the parting agent, for example, alumina. The dry spheroids and parting agent may be mixed in a tumbling mixer such as a twin shell mixer or a cement mixer. The amount of parting agent usually ranges from 3 to 50 weight percent of the material fed to the kiln. Magnesium oxide, zircon, diaspore and high alumina clays may also be useful parting agents as discussed above, as well as other surface metal oxides.

The following are examples of specific metal oxides that may be used as parting agents in the present invention: alumina (less than 45 micrometers particle size obtained as A-2 alumina from Alcoa), magnesium oxide obtained as M-51 MgO from Fisher Scientific Company, and zircon (less than 45 micrometers particle size obtained from NL Industries). Aluminum and magnesium salts convert to oxides at elevated temperatures (e.g., $Al(OH)_3$ and $MgCO_3$ may be substituted for $Al_2O_3$ and MgO in mole equivalent amount). The particle size distribution of the parting agent depends on the desired end product.

The next step is to feed, typically by means of a vibratory feeder, the mixture of parting agent and dry spheroids to a rotary kiln. Firing may be done statically, but a rotary kiln is the preferred apparatus for this step. The residence time of the spheroids in a rotary kiln is dependent upon several parameters: kiln length, diameter, angle, and rotational speed, feed rate to the kiln, temperature within the kiln, gas atmosphere, and diameter of the spheroids. Residence time and temperature are adjusted to achieve the desired properties with each specific formulation for a given end use. With a typical residence time in a rotary kiln of 20 minutes or more, increasing the kiln temperature results in decreasing fired density of the spheroids. Firing temperature is typically above 1100° C.

The ceramic spheroids are overfired, which allows for the formation of the internal air cells, making the finished product less dense. The firing atmosphere is air. The silicon carbide in the spheroids is oxidized during firing, the SiC near the surface being more extensively oxidized than that in the core.

Some of the metal oxide parting agent (e.g., alumina or magnesia) becomes part of the spheroids during the firing step. Metal oxide (e.g. $Al_2O_3$ or MgO) or a metal oxide precursor (e.g. $MgCO_3$ or $Al(OH_3)$) which converts to the metal oxide during firing, is incorporated into the spheroids as they pass through the kiln. Higher firing temperatures result in a thicker shell of parting agent on the spheroids. The coarser the particle size of the mineral particulate in the composition, the higher the required temperature, and more metal oxide is absorbed into the spheroids during firing to form an outer shell rich in metal oxide. Also, finer particle size distribution of the parting agent allows more metal oxide to be absorbed into the spheroids.

The use of metal oxides as parting agents is important for imparting an electrical net charge on the ceramic media particles. The electrical charge can be tailored depending on the metal oxides used in making the particles to have an electrical affinity for particulate matter. Ceramic particles having an electrical affinity for particulate matter that are suitable for the present invention are described in pending U.S. Pat. No. 6,054,059.

In addition to providing the filtration material with a desired electrical affinity, the surface metal oxides serve as parting agents that prevent the prills from sticking together as the intense heat is applied during firing. The surface metal oxides are located on the surface of each particle. However, the surfaces of the particles may not be composed entirely of the surface metal oxides. During firing, some of the surface may be occupied by the surface metal oxides and other portions of the surface may be occupied by the mineral fines. If magnesium oxide is used, a higher percentage of magnesium oxide on the surface may be required compared to the amount of aluminum oxide on the surface.

One example of ceramic filtration material having an electrical charge suitable for use in the present invention comprises the following composition (in % by weight): 96% mineral fines, which may be obtained from Minnesota Mining and Manufacturing Company; 3% bentonite clay, which may be obtained from the American Colloid Company; 1% silicon carbide, which may be obtained from Minnesota Mining and Manufacturing Company; and 14% water.

The dry raw materials are mixed with the water and agglomerated into "prills" having a desired size, with time and percentage of water being variable. The term "prill" as used herein means green or unfired particles of filtration material. The wet prills are dried in a rotating cylindrical gas heated drier. The particles are not completely dried, but are dried enough to be able to be screened and stored.

In a screening process, "on-size" material of desired size is separated from "off-size" material. The off-size material is recycled into the prilling process and the "on-size" material is stored in bulk bags. The on-size prills are proportionally mixed with the surface metal oxide, for example, aluminum oxide, and fed into a kiln.

In the firing stage, the on-size prills are heated in a kiln at a temperature ranging from about 2000 to 2200° F. A kiln that is 4 feet in diameter, 40 feet in length and set at an adjustable incline may be used. The kiln is preferably direct fired with gas as the fuel. The prills are introduced at the higher end of the kiln and as the kiln is rotated, they slowly travel to the lower end of the kiln. A gas burner is located in the center of the lower end of the kiln, which allows a flame to travel along the elongated horizontal axis of the kiln to produce the required temperature. An indirect fired kiln having gas jets disposed outside of the rotating cylinder may also be suitable for making the filtration material of the present invention.

Temperature and rotation are the variables during firing that are used to adjust the specific gravity of the material, as well as to produce different sizes of filtration material. The silicon carbide is involved in a reaction during firing that produces trapped gas within the particles. As a result of this reaction, the specific gravity of the particles may be adjusted as desired. For example, if a lower specific gravity is desired, the material is present in the kiln for a longer time and higher temperature, which generates more trapped gases. If a higher specific gravity is desired, the material spends less time in the kiln at a lower temperature. This enables a wide range of specific gravities and particle sizes of the filtration material to be produced. Specific temperatures and firing times vary with the particular composition of the material and desired specific gravity, but would be apparent by empirical observation to one skilled in the art in view of this disclosure.

Adjusting the specific gravity of the particles is important for gradient filters of the present invention. Of course, the specific gravity of the media for other filter configurations may not be of significance and will be apparent to one skilled in the art in view of the intended application for the filter. In gradient filters, each media layer has preferably a different specific gravity. More preferably, the difference in specific gravity between each ceramic media layer is at least 0.4 units or greater. This differential is important to prevent intermixing of the media layers during filtering and backwashing.

The specific gravities of the ceramic, glass or other particles are typically selected depending on the filter configuration. In a downflow configuration, the smallest particles would have the highest specific gravity whereas in an upflow configuration the smallest particles would have the lowest specific gravity. Specific gravity can be determined as is known by those skilled in the art by weighing a sample, measuring the volume of the sample with an air comparison pycnometer and calculating the weight per cubic centimeter. Alternatively, specific gravity can be calculated by determining the bulk volume density based on percent filling of the total volume by spheres, also known by those skilled in the art as the packing factor.

The product from the kiln is screened using standard methods known to those skilled in the art. The filtration material of the present invention has a final particle size range depending on the sieves used, for example, 20/40 and 30/50, which means that substantially all particles have a size ranging from 20 to 40 mesh (841–420 micron in diameter) and 30 to 50 mesh (595–297 micron in diameter), respectively. The particle size fraction is preferably not larger than about 10 mesh (about 2000 micron in diameter) and, as small as about 80 mesh (about 177 micron in diameter). The particle size is preferably selected, depending upon the composition of filtration material, to provide the material with electrical affinity characteristics that are suitable for removing particles about 3 micron and less. In many cases, the particle size of the ceramic material is much smaller than 20 mesh, for example, about 70/80 mesh. Ceramic particles of a size of not greater than 10 mesh and preferably about 80 mesh are used in the present invention. 80 mesh ceramic particles are able to remove particles about 3 micron and less from the feed liquid through a combination of physical straining and electrical affinity mechanisms. These small ceramic particles pack more closely together than larger particles and have a greater surface area, which increases the electrical affinity effect. Ceramic particles that do not exhibit the electrical affinity effect may also be used in the gradient filter of the present invention.

Either before, during or after the screening step, the fired spheroids may be subjected to vigorous agitation by air or some other agitation means or to a water washing step in order to remove dust from their surfaces.

Other types of media suitable for use in the present invention include polymeric media such as beads of polypropylene, polycarbonate, polyacrylates, polyesters and the like, inorganic media such as silicate aggregates and the like, and crystalline microporous materials such as zeolites.

The following examples are detailed description of methods of preparation and use of the composition of the present invention. The detailed preparations fall within the scope of, and serve to exemplify, the more generally described methods set forth above. The examples are presented for illustrative purposes only, and are not intended to limit the scope of the invention.

EXAMPLE 1

In this example, a grafting solution is prepared as follows:

| COMPONENTS | Parts by Weight | |
|---|---|---|
| PART A | | |
| Epoxy Prepolymer (EPON 828) | 500 | |
| Propylene Glycol Methyl Ether | 100 | |
| AP Silane 99 | | 5 |
| Acetone | | 1000 |
| Polyethylene Glycol Diacrylate (SR344) | 1 | |
| ZINC OMADINE | | 15 |
| AMICAL 48 | | 20 |
| 1% Methyl Ethyl Ketone Peroxide in MEK | | 0.01 |
| 1% Silver Perchlorate in water | 0.001 | |

-continued

| COMPONENTS | Parts by Weight | |
|---|---|---|
| PART B | | |
| ANCAMINE TETA | | 70 |
| Propylene glycol Methyl Ether | 51 | |
| Acetone | | 300 |

The components of Part A were combined and mixed to a uniform solution. Part B, containing the polymerization catalyst, was prepared separately from Part A and subsequently mixed with Part A prior to use. The mixing ratio by weight is 38.9 parts of Part A to 10 parts of Part B. The grafting solution is then ready for use.

EXAMPLE 2

In this example, a grafting solution is prepared according to example 1 as follows:

| COMPONENTS | Parts by Weight | |
|---|---|---|
| PART A | | |
| Epoxy Prepolymer (EPON 828) | 580 | |
| Propylene Glycol Methyl Ether | 141 | |
| AP Silane 99 | | 6 |
| Acetone | | 1,624 |
| Polyethylene Glycol Diacrylate (SR344) | 1 | |
| ZINC OMADINE | | 42 |
| AMICAL 48 | | 15 |
| 1% Methyl Ethyl Ketone Peroxide in MEK | | 0.01 |
| 1% Silver Perchlorate in water | 0.001 | |
| PART B | | |
| ANCAMINE TETA | | 70 |
| Propylene glycol Methyl Ether | 51 | |
| Acetone | | 464 |

The mixing ratio by weight is 41.2 parts of Part A to 10 parts of Part B.

EXAMPLE 3

In this example, ceramic filtration media was prepared by combining 45 lbs. bentonite, 1440 lbs. nepheline syenite, and 15 lbs. silicon carbide. To this was added 15% by weight water. The combination was then mixed at a high speed in an Eirich mixer to form spheroids. The wet spheroids are then discharged from the Eirich mixer and dried at a temperature of about 93 ° C. The dried spheroids are screened to obtain a desired mesh size.

The spheroids are then mixed with a fine powder (−325 mesh) of an aluminum oxide parting agent The amount of parting agent used was about 200 lbs. The spheroids were then fired at 1200° C. for about 20 minutes. After firing, the spheroids are cooled and agitated by air to remove dust. The spheroids are then sorted by mesh size prior to use as ceramic filtration media. In this example, 70–80 mesh fired spheroids were collected and used as the filtration media in the following examples.

EXAMPLE 4

In this example, the grafting solution of Example 1 was slowly added to the ceramic filtration media of Example 3 to completely cover and wet the ceramic media. The amount of grafting solution added should be sufficient to completely cover and wet the ceramic media. The contents are stirred and then filtered. The treated (wet) media is then stir dried for an additional 24 hours and finally, cured at 70° C. for 2 hours. The resulting cured filter media is ready for use as germicidal filter media.

EXAMPLE 5

In this example, the grafting solution of Example 2 was slowly added to the ceramic filtration media of Example 3 to completely cover and wet the ceramic media. The amount of grafting solution added should be sufficient to completely cover and wet the ceramic media. The contents are stirred and then filtered. The treated (wet) media is stir dried for an additional 24 hours and finally, cured at 70° C. for 2 hours. The resulting cured filter media is ready for use as germicidal filter media.

EXAMPLE 6

In this example, the germicidal filter media of Examples 4 and 5 were packed into 500-milliliter glass column drinking water treatment units (DATUM) and conditioned. Each DWTU was tested initially using a theoretical contact time of thirty minutes. *Klebsiella terregina* was selected as the challenge organism for these trials. Challenge organism doses were propagated in accordance with the procedures outlined in the EPA Guide Standard and Protocol for Testing Microbiological Water Purifiers. The challenge dose was $1 \times 10^5$ colony forming units per milliliter (CFU/ml). The target reduction was greater than or equal to four ($10^4$) log (~99.99%). Due to the low flow rate, the challenge organisms were seeded into a continuously mixing challenge reservoir rather than injected into the system flow. Influent (pretreatment) and effluent (post-treatment) samples were collected and analyzed for bacterial enumeration to document DWTU performance. Influent samples were collected as grab samples from the reservoir at the beginning, middle and end of the challenge period. The influent samples were composited for analysis, yielding a single pretreatment sample. The flow rate of the feed liquid was approximately 17 milliliters per minute. Flow was continuous during the test periods. System pressure was less than ten pounds per square inch gauge (psig). Each DWTU was tested three times to allow for an assessment of variability. The three trials were performed sequentially, with a fifteen-minute flushing period in between trials. One negative control sample was collected prior to each trial. The entire effluent flow was collected by filtration (0.45um, sterile filters). All samples were analyzed in triplicate in accordance with standard procedures. The results are shown in Table I.

TABLE I

| Media Sample No. | Average $Log_{10}$ Reduction Value |
|---|---|
| Example 4 | >8.1 |
| Example 5 | 7.2 |

The results indicate excellent removal, deactivation and destruction of *Klebsiella terregina* by the germicidal grafted filter media of Examples 4, and 5.

EXAMPLE 7

In this example, three trials were sequentially performed on each DWTU containing the filter media of examples 4 and 5 to assess the variability in performance and the effectiveness of the media after repeated use. Prior to propagation of the challenge dose, the challenge organism, *Klebsiella terregina*, was identified using a Biolog bacterial identification system. Challenge doses were then propagated from a single colony of *Klebsiella terregina*. One negative control sample was collected from the effluent sample port prior to each trial. The control sample was analyzed concurrently with the influent and effluent samples. In addition, water remaining in the challenge reservoir after completion of each trial was sampled and analyzed. These data were not used in the reduction calculations, but were to ensure that a disproportionate percentage of the challenge dose does not remain in the reservoir. Influent samples served as positive control samples documenting recovery of target organisms. The results are shown in Table II.

TABLE II

| Media Example No. | Run No. | Average Influent Colony Forming Unit | Average Effluent Colony Forming Unit | $Log_{10}$ Reduction |
|---|---|---|---|---|
| 4 | 1 | 1.6E+08 | <1 | >8.2 |
| 4 | 2 | 1.3E+08 | <1 | >8.0 |
| 4 | 3 | 1.0E+08 | <1 | >8.1 |
| 5 | 1 | 2.0E+08 | 25 | 6.9 |
| 5 | 2 | 1.8E+08 | 11 | 7.2 |
| 5 | 3 | 1.8E+08 | 7 | 7.4 |

The results clearly indicate the efficiency of the germicidal grafted filter media for removing, deactivating, and/or destroying the challenge organisms. More importantly, the data suggests that the media is stable and the germicidal activity is sustained after repeated use.

EXAMPLE 8

In this example, the effect of contact time with the media of examples 4 and 5 was measured. Influent concentrations were between 2 and 4 million CFU/ml. The heterotrophic plate count, formerly known as the standard plate count, was the procedure used for estimating the number of live heterotrophic bacteria in the water samples. The colonies measured by this method include pairs, chains, clusters or single cell bacteria, all of which are included in the term "colony forming unit". The results are shown in table III.

TABLE III

| Empty Bed Contact Time (seconds) | Example 4, $Log_{10}$ reduction | Example 5, $Log_{10}$ reduction |
|---|---|---|
| 20 | 2.6 | 2.2 |
| 30 | 2.1 | 2.5 |
| 60 | 2.4 | 2.5 |
| 100 | 3.1 | 4.9 |
| 150 | 5.3 | 5.3 |
| 200 | 5.6 | 5.4 |
| 300 | 5.3 | 5.3 |
| 600 | 5.5 | 5.3 |

The results indicate that contact times of the influent with the media for about 150 seconds and greater resulted in an effluent with less than 10 CFU/ml. It is important to note that the detection limit for this method is 10 CFU/ml, so the maximum log reduction possible for these test was 5.6. Contact times greater than 150 seconds showed a significant reduction in influent versus effluent CFUs.

EXAMPLE 9

In this example, the effectiveness of the filter media for destroying, deactivating and/or removing viruses was determined. Filters containing the filter media of examples 4 and 5 were prepared in accordance with example 6. MS2 bacteriophage challenge organisms were propagated in accordance with the procedures outlined in EPA Guide Standard and Protocol for testing Microbiological Water Purifiers. The Guide Standard indicates $1 \times 10^7$ plaque forming units per milliliter (PFU/ml) as the challenge dose. Effluent samples were collected by sterile pipette and analyzed by the double agar overlay method. *E. Coli* was used as the bacterial host to enumerate bacteriophage MS2. The results are shown in table IV.

TABLE IV

| Media | Average Applied Dose (PFU/mL) | Average Effluent Count (PFU/mL) | $Log_{10}$ Reduction Value |
|---|---|---|---|
| Example 4 | 6.8E+06 | <0.33 | >7.31 |
| Example 4 | 8.9E+06 | 0.33 | 7.43 |
| Example 4 | 7.6E+06 | <0.33 | >7.36 |
| Example 5 | 6.1E+06 | <0.33 | >7.27 |
| Example 5 | 8.5E+06 | <0.33 | >7.41 |
| Example 5 | 1.2E+06 | <0.33 | >7.56 |

The media tested achieved consistently excellent log removals of under the experimental conditions outlined. All negative control samples collected from the effluent sample port prior to each trial were negative for MS2. Seeded influent samples (pretreatment) were positive for MS2. The results demonstrate the effectiveness for removing and/or destroying the MS2 bacteriophages from the feed liquid.

EXAMPLE 10

In this example, 100 grams of the filter media (example 3) and 100 grams of the germicidal media (examples 4 and 5) was added to 1 liter of water to determine whether the germicidal polymer leached from the media into the water after a period of exposure and agitation. The pH and conductivity were measured after 1 hour and after 20 hours of continuous stirring. The results are shown in table V.

TABLE V

| | pH | | Conductivity ($\mu$S/cm) | |
|---|---|---|---|---|
| Media | 1 hour | 20 hours | 1 hour | 20 hours |
| Example 3 | 8.11 | 9.06 | 24 | 54 |
| Example 4 | 8.84 | 8.88 | 98 | 124 |
| Example 5 | 9.15 | 9.04 | 176 | 202 |

The results show that conductivity increase was negligible for the germicidal filter media compared to the filter media after 20 hours of continuous stirring. The measured pH for the germicidal grafted media was relatively constant These results indicate that the germicidal polymer is tightly bound to the media and after extended agitation will not be easily removed.

Many modifications and variations of the invention will be apparent to those skilled in the art in light of the foregoing disclosure. Therefore, it is to be understood that, within the scope of the appended claims, the invention can be practiced otherwise than has been specifically shown and described.

What is claimed is:

1. Synthetic filtration media having germicidal properties for use in filtering particles and simultaneously destroying, removing and/or deactivating microorganisms from a feed liquid passing therethrough, said synthetic filtration media having chemically grafted and covalently bonded thereto polymerizable monomers, to which at least one germicide is associated, a curing agent, and a surface agent.

2. The filtration media according to claim 1 wherein the said filtration media is selected from the group consisting of ceramic spheroids, wherein, ceramic spheroids comprising metal oxides embedded onto an outer surface of said spheroid, glass hollow spheres, and glass hollow spheres comprising silicates and phenol embedded in the wall of said hollow spheres.

3. The filtration media according to claim 1 wherein at least two germicides are associated to said polymerizable monomers.

4. The filtration media according to claim 1 wherein said polymerizable monomers and said germicides are present in a range of molar ratios, from ratios of 100:1 to 1:100.

5. The filtration media according to claim 1 wherein said polymerizable monomers and said germicides are present in about a 1:1 molar ratio.

6. The filtration media according to claim 1 wherein each said germicide has a minimum inhibitory concentration less than about 1000 ppm for at least one targeted microorganism.

7. The filtration media according to claim 1 wherein each said germicide has a minimum inhibitory concentration less than about 10 ppm for *Staph. Aureus*.

8. The filtration media according to claim 1 wherein one said germicide is a bisguanidine.

9. The filtration media according to claim 1 wherein said germicides are selected from the group consisting of zinc pyrithione and diiodomethyl-p-tolylsulfone.

10. The filtration media according to claim 1 wherein said polymerizable monomer is selected from the group consisting of vinyl and acrylic monomers.

11. The filtration media according to claim 10 wherein said polymerizable monomer includes a carboxyl group.

12. The filtration media according to claim 10 wherein said polymerizable monomer includes a sulfonyl group.

13. The filtration media according to claim 1 wherein said surface agent is n-hexyl trimethoxysilane.

14. The filtration media according to claim 1 wherein said cuing agent is an aliphatic amine.

15. The filtration media according to claim 1 wherein said monomer and said germicides are copolymerized with at least one monomer wherein the amount of said secondary monomer is at least 10 percent of the amount of said primary monomer.

16. The filtration media according to claim 1 wherein said feed liquid comprises water.

17. A method of preparing syntheic germicidal filter media comprising:
   a) preparing a grafting solution comprising mixing to a uniform solution at least one germicide, at least one monomer, a catalyst for initiating polymerization, a curing agent, a surface agent, and at least one graft initiator in a solvent;
   b) contacting said grafting solution with a synthetic filtration media to form a mixture;
   c) Removing any excess grafting solution from said mixture to obtain wet synthetic filtration media;
   d) air drying wet synthetic filtration media; and
   e) curing said synthetic filtration media at an elevated temperature effective to chemically graft and covalently bond to a surface of said filtration media polymerized monomers and at least two germicides associated thereto.

18. The method according to claim 17 wherein at least two germicides are used in the preparation of said grafting solution.

19. The method according to claim 17 wherein said filtration media is chosen from the group consisting of ceramic spheroids, wherein, ceramic spheroids comprising metal oxides embedded onto an outer surface of said spheroid, glass hollow spheres, and glass hollow spheres comprising silicates and phenol embedded in the wall of said hollow spheres.

20. The method of claim 17 wherein said grafting solution further comprises at least one other secondary polymerizable monomer co-polymerizable with the primary monomer.

21. The method of claim 17 wherein the amount of said secondary monomer is at least 10 percent of the amount of said primary polymerizable monomer.

22. The method of claim 17 wherein a molar ratio of said polymerizable monomers and said germicides are present in a range of molar ratios, from ratios of 100:1 to 1:100.

23. The method of claim 17 wherein a molar ratio of said polymerizable monomers and said germicides are present in about a 1:1 molar ratio.

24. The method of claim 17 wherein said graft initiator is selected from the group consisting of silver, ferrous and ferric ions.

25. The method of claim 17 wherein said catalyst is selected from the group consisting of a hydrogen peroxide, a methyl ethyl ketone peroxide, a urea peroxide and an ammonium persulfate.

26. A method for purifying an aqueous based feed liquid comprising flowing source feed liquid across synthetic filter media which has chemically grafted thereto polymerized monomers and at least one germicide associated thereto whereby said synthetic filter media removes particles and destroys ,removes and/or deactivates microorganism in the liquid.

27. The method according to claim 26 wherein the said filtration media is chosen from the group consisting of ceramic spheroids, ceramic spheroids comprising metal oxides embedded onto an outer surface of said spheroid, glass hollow spheres, and glass hollow spheres comprising silicates and phenol embedded in the wall of the hollow spheres.

28. The method of claim 26 wherein the filter media and the source water are free from chemical coagulants.

29. A filtration apparatus for filtering particles and destroying, removing and/or deactivating microorganisms from a feed liquid comprising a flow path, and synthetic germicidal filter material disposed in the flow path, said synthetic filtration material having chemically grafted thereto polymerized monomers and at least one germicide associated thereto whereby the synthetic filter material is effective for removing particles and is effective for destroying, removing and/or deactivating microorganisms from the feed liquid.

30. Filtration media having germicidal properties for use in filtering particles and simultaneously destroying, removing and/or deactivating microorganisms from a feed liquid passing therethrough, said filtration media having chemically grafted and covalently bonded thereto polymerizable monomers, to which at least one germicide is associated, a curing agent, and a surface agent, wherein said surface agent is n-hexyl trimethoxysilane.

31. Filtration media having germicidal properties for use in filtering particles and simultaneously destroying, removing and/or deactivating microorganisms from a feed liquid passing therethrough, said filtration media having chemically grafted and covalently bonded thereto polymerizable monomers, to which at least one germicide is associated, a curing agent, and a surface agent, wherein said surface agent is an aliphatic amine.

* * * * *